United States Patent [19]
Soranzo et al.

[11] Patent Number: 6,110,208
[45] Date of Patent: Aug. 29, 2000

[54] ARTIFICIAL SKIN CONTAINING AS SUPPORT BIOCOMPATIBLE MATERIALS BASED ON HYALURONIC ACID DERIVATIVES

[75] Inventors: Carlo Soranzo; Giovanni Abatangelo, both of Padova; Lanfranco Callegaro, Vicenza, all of Italy

[73] Assignee: Fidia Advanced Biopolymers S.R.L, Italy

[21] Appl. No.: 08/955,796

[22] PCT Filed: Apr. 25, 1996

[86] PCT No.: PCT/EP96/01734

§ 371 Date: Oct. 22, 1997

§ 102(e) Date: Oct. 22, 1997

[87] PCT Pub. No.: WO96/33750

PCT Pub. Date: Oct. 31, 1996

[30] Foreign Application Priority Data

Apr. 27, 1995 [IT] Italy .................................. PD95A0083

[51] Int. Cl.[7] ........................................................ A61F 2/10
[52] U.S. Cl. .............................. 623/15; 623/66; 424/422
[58] Field of Search ........................ 623/15, 66; 128/898; 424/422, 423, 424, 425, 426

[56] References Cited

U.S. PATENT DOCUMENTS

| | | | |
|---|---|---|---|
| 4,485,096 | 11/1984 | Bell | 424/95 |
| 5,326,356 | 7/1994 | Della Valle et al. . | |
| 5,650,164 | 7/1997 | Valle et al | 424/422 |
| 5,658,331 | 8/1997 | Valle et al. | 623/15 |

FOREIGN PATENT DOCUMENTS

| | | |
|---|---|---|
| 0216453 | 4/1986 | European Pat. Off. . |
| WO9311803 | 6/1993 | WIPO . |

OTHER PUBLICATIONS

The New England Journal of Medicine, vol. 311, No. 7, pp. 448–451, Aug. 1984, "Permanent Coverage of Large Burn Wounds With Autologous Cultured Human Epitherlium", Gallico, III, M.D. et al.

Science, vol. 215, No. 8, pp. 174–176, Jan. 1982, "Wound Tissue Can Utilize a Polymeric Template to Synthesize a Functional Extension of Skin".

Surgery, vol. 103, No. 4, pp. 421–431, Apr. 1988, "Biologic Attachment, Growth, and Differentiation of Cultured Human Epidermal Keratinocytes on a Graftable Collagen and Chondroitin–6–Sulfate Substrate", Boyce, Ph.D., et al.

The Society for Investigative Dermatology, Inc., vol. 91, No. 5, pp. 478–485, Nov. 1988, "Reconstitution of Structure and Cell Function in Human Skin Grafts Derived From Cryopreserved Allogeneic Dermis and Autologous Cultured Keratinocytes", Langdon, M.D., et al.

Abstract, American Society for Aestheric Plastic Surgery, Inc., p. 80, Jan.–Mar. 1995.

In Vitro Cellular & Developmental Biology, vol. 22, No. 12, pp. 695–705, Dec. 1986, "Keratinocytes Grown at the Air–Liquid Interface", Bernstam et al.

Cell, 6:331–344, Nov. 1975, "Serial Cultivation of Strains of Human Epidermal Karatinocytes: The Formation of Keratinizing Colonies From Single Cells", Rheinwald et al.

*Primary Examiner*—Mickey Yu
*Assistant Examiner*—Dinh X. Nguyen
*Attorney, Agent, or Firm*—Hedman, Gibson & Costigan, P.C.

[57] ABSTRACT

Artificial human skin is disclosed which is based on: (a) a microperforated membrane based on a hyaluronic acid derivative on which keratinocytes have been seeded and cultured; (b) an underlying non-woven tissue based on a hyaluronic acid derivative wherein fibroblasts have been seeded and left to proliferate.

The artificial human skin may be used in medical, surgical, diagnostic and controlled release drug delivery applications. The artificial human skin may be safely frozen to –80° C. or stored in liquid nitrogen in order to have a skin tissue bank.

24 Claims, 7 Drawing Sheets

OTHER PUBLICATIONS

The Journal of Cell Biology, vol. 113, No. 1, pp. 207–221, Apr. 1991, "Human Keratinocytes Express a New CD44 Core Protein (CD44E) as a Heparan–Sulfate Intrinsic Membrane Proteoglyca with Additional Exons", Brown et al.

The Journal of Cell Biology, vol. 111, No. 6, Pt. 1, pp. 2765–2774, Dec. 1990, "The Hyaluronate Receptor is a Member of the CD44 (H–CAM) Family of Cell Surface Glycoproteins", Culty et al.

Developmental Biology, vol. 155, 324–336, 1993, CD44 Positive Macrophages Take Up Hyaluronan During Lung Development Underhill et al.

The Society for Investigative Dermatology, Inc., vol. 101, No. 4, pp. 634–638, Oct. 1993, "Human Hair Follicle Germinative Epidermal Cell Culture", Reynolds et al.

Proc. Nat'l. Acad. Sci. USA, vol. 76, No. 11, pp. 5565–5669, Nov. 1979, "Growth of Cultured Human Epidermal Cells Into Multiple Epithelia Suitable for Grafing", Green et al.

Wounds, vol. 3, No. 3, pp. 116–126, May–Jun. 1991, "Human Keratinocytes Cultured on Membranes Composed of Benzyl of Hyaluronic Acid Suitable for Grafting", Andreassi et al.

The Journal of Investigative Dermatology, 81:74s–81s, 1983, "Keratinocytes Synthesized Basal–Lamina Proteins in Culture", Prunieras et al.

ARTIFICIAL SKIN CONTAINING AS SUPPORT BIOCOMPATIBLE MATERIALS BASED ON HYALURONIC ACID DERIVATIVES

FIELD OF THE INVENTION

The present invention relates to:

an artificial human skin constituted by a completely differentiated epidermis and dermal appendage, and containing as the support two biocompatible materials based on hyaluronic acid (HA) derivatives the processes for preparing this artificial human skin, the use of this artificial skin in medicine and in surgery, as a diagnostic device, and as vehicling agent for preparing controlled release medicament.

BACKGROUND OF THE INVENTION

Skin loss due to trauma or disease is usually treated by the autograft technique, that is, by substituting the missing skin with pieces taken from donor areas of the same patient. An important step forward in the treatment of such lesions by reconstructive surgery is represented by in vitro cultures of keratinocytes (kc) (J. Rheinwald and H. Green, Cell, 6:331, 1975), whereby said cultures are allowed to expand in vitro, and membranes of epidermal cells are obtained which are potentially useful to cover skin wounds. This technique has been widely used in clinical practice, mainly for burn patients (G. G. Gallico et al., M. Engl.J. Med., 311–448, 1984), but problems arose right from the start, such as the difficulty for such grafts to take, the fragility of the epithelial sheets and consequent difficulty for the surgeon to handle them.

A different approach was adopted by Yannas et al. (Science, 215:174, 1982), who used resorbable porous materials constituted by coprecipitates of collagen and glycosaminoglycans (GAG), particularly chondroitin-6-sulphate, covered by a thin film of silicon membrane. The characteristic of such materials is that they present randomly formed, intercommunicating pores, rather like a sponge.

S. Boyce and J. Hansbrough (Surgery, 103–421, 1988) described growing kc on the surface of membranes made of collagen and GAG, reducing the surface porosity of the material. In order to limit the development of epidermal culture on the membrane surface, an additional, non-porous layer was inserted.

Skin graft technology must take into consideration the interaction between kc, the basal membrane and the underlying dermis. Nowadays it is generally thought that in the case of full-thickness lesions, autografts can be notably facilitated by placing a dermal bed in the wound underneath the epithelial layer.

The basal kc thus lie on a more physiological substrate and can develop a basal membrane and dermal-epidermal linking structures, capable of lending the necessary resistance to the graft.

Recent clinical studies have suggested that Cuono's method (Langdon et al. J. Invest. Dermatol. 91 5: 478, 1988), whereby a "full-thickness" wound is treated with an allograft from the skin of a cadaver, gives better results in terms of the percentage of graft which takes and general quality of the skin on healing.

However, grafts are difficult to obtain, expensive to store and are potential carriers of pathogenic viruses.

There is clearly a need for new, biodegradable, artificial skin substitutes which do not have these drawbacks, and satisfy the following requirements:

1) their surfaces must allow for adhesion and cell growth;
2) neither the polymers themselves, nor their degradation products should cause inflammation or toxic phenomena when implanted in vivo;
3) the product should be perfectly reproducible in its three dimensions;
4) its ideal porosity is 50%, which gives a large surface area for cell-polymer interactions, sufficient volume for the deposit of extracellular matrix and only slight, or no, migrational impediments during in vitro culture.
5) the supporting polymer should be absorbed once the regenerated tissue no longer requires it. Indeed, foreign bodies in vivo represent a high risk of infection and/or inflammation.

Indeed, the products already on the market or being developed present certain drawbacks: their degradation is uncontrollable and interferes with the wound healing process, thus favouring inflammation. Moreover, these substitutes require the epithelial cells to be thickly seeded on the support and left to proliferate for a long time.

Some examples of the products known to date and generally recommended for use in treatment of severe burns are:

1) Dermagraft®, developed by ATS (California), wherein heterologous human fibroblasts are cultivated on a spongy, resorbable material constituted by polylactic, polyglycol or polygalactoside acid. Autologous kc are seeded onto these materials;
2) GraftSkin®, produced by Organogenesis Inc. (Boston, USA), wherein heterologous human fibroblasts are cultivated on a collagen based substrate;
3) AlloDerm®, produced by Life Cell Corp. (Texas, USA) and based on human or pigs' skin, wherein the basal membrane and dermal matrix remain intact. The tissue is stored at a low temperature (−80° C.) until ready to be used, when it is seeded with autologous fibroblasts and kc and then grafted into the patient.

However, these, and other products do not allow the in vitro reconstruction of a perfectly functional dermoepidermal junction.

The use of hyaluronic acid (HA) derivatives has also been described (EPA. 0216453) for the preparation of suitable products, particularly membranes to support human kc growth (EPA 0462426) and non-woven tissues (WO 93/11803). Abatangelo et al. (Wound Repair and Regeneration, January–March, p. 80, 1995) reported the use of nonwoven tissue to support mixed cultures of human kc/fibroblasts. Even so, the epithelial layer was not homogeneous because of the kc which seeded in the gaps in the non-woven tissue, thus giving it an uneven thickness. Degradation of the polymers considered here mainly produces hyaluronic acid (HA), which is a normal constituent of the extracellular matrix and therefore has the advantage of being metabolized by normal cell mechanisms.

The chemical modifications allow the product to remain at the site of the graft for far longer than is possible with the natural polymer, and the receptor interactions are maintained throughout that time. In this regard, it must be remembered that the main receptor for HA, known as CD44, is normally expressed in the epithelial tissues, particularly in the basal and spinous layers of the epidermis, while expression of the protein gradually decreases in the upper layers until it disappears in the completely differentiated kc (Carter et al., J. Cell Biol. 113207, 1991). Moreover, the role of CD44 in HA's degradation mechanism is well documented (Culty et al. J. Cell. Biol. 111:2765, 1990; Underhill, Dev. Biol. 155:324, 1993).

The purpose of the present invention is an artificial human skin simulating both the epidermal and dermal layer of the natural one, wherein both fibroblasts and keratinocytes (kc) are present, both cell types actively proliferating and separated, at the interface, by a protein extracellular matrix, having the characteristic of a dermoepidermal junction.

SUMMARY OF THE INVENTION

The Applicant has therefore unexpectedly found the artificial human skin subject of the present invention which comprises:

a) a microperforated membrane based on a hyaluronic acid derivative, on which keratinocytes have been seeded and cultured, b) an underlying non-woven tissue based on a hyaluronic acid derivative wherein fibroblasts have been seeded and left to proliferate.

The artificial skin, subject of the present invention generally further comprises an extracellular protein matrix containing proteins of the dermo-epidermal junction, placed at the interface between keratinocytes and fibroblasts.

Thanks to its biodegradability, which can also be a result of the receptor mechanism mentioned previously, the artificial human skin is spontaneously absorbed within a set time, leaving just the newly-formed tissue at the lesion site.

Therefore the artificial human skin according to the present invention can be advantageously used in medicine and in surgery.

In addition the artificial human skin can be advantageously used as a vehicle for preparing controlled release medicaments containing at least one active principle selected from the group consisting of biologically active compounds, proteins, peptides and mixtures thereof, wherein said active principle is adsorbed to the fibres of the non-woven tissues and/or to the microperforated membrane.

Moreover, it is possible to use artificial skin as a diagnostic device for in vitro tests to verify the possible toxic effect of products and/or substances destined to be placed in contact with the skin and to be used in the chemical, pharmaceutical, cosmetic and agricultural fields.

The artificial skin can be also advantageously used in the cosmetic field in particular for hair graft.

In fact dermal hair follicle fibroblasts can be used along with keratinocytes isolated from the same region in order to build up an organotypic culture showing features of the "in vivo" site of origin as described in "Human Hair Follicle Germinative Epidermal Cell Culture"

Amanda J. Reynolds et al. Rapid Communication pp. 634–638.

Lastly, a further advantage of the artificial human skin is that it can be frozen to −80° C. or placed in liquid nitrogen and stored, so that a tissue bank can be created, thus enabling immediate grafts whenever and wherever needed, as the product can thus be constantly available, even in centres which are not specialized in dermoepidermal cultures.

A further object of the present invention resides in the processes for preparing said human artificial skin.

In particular the first process comprises the following steps:

i) seeding keratinocytes cultures at a density ranging from 1,000 to 100,000 cell/cm$^2$, on the microperforated membranes and expanding the Kc on said membrane. The conventional culture technique involving the use of Fetal Calf Serum (FCS) is followed until partial or complete confluence is achieved.

ii) cultivating the fibroblasts isolated from the dermis or from other districts by the usual techniques in DMEM containing 10% fetal calf serum, conditioning these fibroblasts to proliferate first by seeding them on plastic, and then seeding the fibroblasts in the non-woven tissue and continuing the culture until freezing, (in case the obtained artificial skin must be preserved) or until grafting, iii) laying the epithelial layer formed on the microperforated membrane on the non-woven tissue colonized by fibroblasts, being careful that the outer edge of the microperforated membrane does not touch the bottom of the dish and that it extends slightly beyond the underlying non-woven tissue, iv) optionally fixing together the epithelial cells layer on the microperforated membrane to the underlying non-woven tissue colonized by fibroblasts by means of biological adhesives selected from the group consisting of: collagen, fibrin, fibrin glue.

v) adding a sufficient volume of the same medium used in step (i), keeping the culture immersed so that the keratinocytes of the upper layer of the microperforated membrane are at the air-liquid interface, adding at the first and subsequent changes of medium, ascorbic acid at concentration equal to 1 $\mu$g/ml, continuing the culture until grafting or freezing.

It is known that keratinocytes can be cultivated in medium free from fetal calf serum and feeder-layer of murine fibroblasts, so the artificial skin, which is the subject of the present invention, can be obtained by the simultaneous seeding of human fibroblasts in the non-woven tissue and of keratinocytes on the membrane. In this case a "chemically defined" medium is used which is suitable, for keratinocyte growth. In this case the process comprises the following steps:

i') seeding the fibroblasts in the non-woven tissue and continuing the culture until freezing or grafting, ii') laying the microperforated membrane on the non-woven tissue, with its edges extending slightly beyond those of the underlying tissue and fixing said membrane with the biological adhesives used in the previous process or by mechanical means, iii') seeding the keratinocytes on the microperforated membrane, expanding said keratinocytes by using said "chemically defined" medium, which is suitable for keratinocyte growth on plastic dishes until confluence is achieved, iv') adding a sufficient volume of the medium used in the preceding step, keeping the culture immersed so that the keratinocytes of the upper layer of the microperforated membrane are on the air-liquid interface, adding at the first and subsequent changes of medium, ascorbic acid at concentration equal to 1 $\mu$g/ml, continuing the culture until grafting.

The above processes according to the present invention comprise a further step consisting of cryopreserving said artificial skin in the presence of a cryopreserving agent, when the skin must be preserved.

DETAILED DESCRIPTION OF THE INVENTION

Figure 1:
FIG. 1 shows Hematoxylin and Eosin staining of a 15-day-old composite dermal-epidermal culture. Kcs have migrated through the Laserskin® membrane to the non-woven tissue, which is embedded with fibroblast cells (×100).

The epithelial layer is reconstructed by seeding human kc on a microperforated membrane, prepared according to U.S. Pat. No. 5,326,356, which we incorporate by reference, while the human fibroblasts are cultivated on a material known as non-woven tissue, as described in the International Patent Application No. WO 93/11803, which we incorporate herewith by reference.

The hyaluronic acid derivative used for preparing both the microperforated membrane and the non-woven fabric is preferably an ester of hyaluronic acid. Preferably these esters have a percentage of esterification comprised between 75% and 100%. By varying the percentage of esterification of the hyaluronic acid esters used, it is possible to control the degradation kinetics of the tissue support and, therefore, the length of time that the device can remain in situ. The preferred hyaluronic acid esters are the benzylesters of hyaluronic acid.

The microperforated membranes of hyaluronic benzylester are in particular already commercially available with the trademark Laserskin®.

Both fibroblasts and keratinocytes are of human origin or of a species which is compatible when grafted into humans.

When both these kinds of cells are of human origin they can be heterologous, autologous or combinations of these two types.

As previously pointed out the human artificial skin subject of the present invention can be advantageously used in medicine and surgery.

In fact the final outcome of the wound healing process is considerably improved, with particular reference to cases of:

1) deep, II and III-degree burns.
2) various kinds of ulcer: diabetic, venous, bedsores;
3) plastic surgery.

Indeed, a physiological covering for these kinds of lesions, albeit composed of heterologous cells, reduces the risk of infection or excessive loss of organic fluids. Moreover, the proliferating cells in the dermal bed secrete substances (still partly unknown) such as growth factors and cytokines, which accelerate the wound healing process.

Moreover the skin according to the present invention can be used for the treatment of diseases characterized by melanine deficiency such as vitiligo.

In this case the artificial human skin of the present invention contains a quota of melanocytes which can be grafted by means of the same skin to patients affected by vitiligo.

The artificial human skin can in particular also be applied in genetic therapy, wherein the cells of a patient (kc, fibroblasts or both) are genetically modified, for example to correct congenital malformations and/or metabolic defects.

When the human artificial skin according to the present invention is used as vehicling agent for preparing controlled release medicaments containing proteins, these are preferably growth factors, such as FGF (Fibroblast Growth Factors), TGF β(Transforming Growth Factor β), KGF (Keratinocyte Growth Factor), NGF (Nerve Growth Factor), proteins involves in the clothing cascade such as Coagulation Factor VIII and others. Moreover, proteins of the extracellular matrix, such as Fibronectin, Laminin, Collagen can be adsorbed to the fibres of the non-woven tissue, to improve the cell attachment process.

In the first process according to the present invention, in step (i) the seeding density of keratinocytes cells is preferably comprised between 5,000 and 25,000 cells/cm$^2$.

The conventional technique used for expanding these keratinocytes and involving the use of fetal calf serum are basically those described by Rheinwald and Green (Cell, 6:331, 1975). In particular CEC culture medium is used (Green H. et al., J. Proc. Nation. Acad. Sci. 76:5665, 1979), in the presence of a "feeder-layer" of nonproliferating 3T3-J2 murine fibroblasts. The mean confluence time is generally comprised between 7–12 days or 15–24 days from the initial setting up of the culture.

In step (i') of the second process the commercially available medium called MCDB 153 (or others) is preferably used as "chemically defined" medium for expanding the keratinocyte cells.

According to the present invention in both the processes primary or defrozen cultures of fibroblasts and keratinocytes can be used.

The cryopreservation step used in both processes for preparing the artificial human skin, when the same must be preserved, is preferably carried out in the presence of dimethylsulfoxide or glycerol as cryopreserving agents.

It is possible to demonstrate that in the artificial human skin according to the present invention kc migrate through the micropores in the membrane, to the upper part of the non-woven tissue in direct contact with the membrane, while the fibroblasts produce a considerable quantity of protein extracellular matrix.

Of considerable interest is also the fact that kc embedded in the non-woven tissue and in contact with the fibroblasts, take on the appearance of epithelioid basal cells, expressing membrane markers typical of the cells in the basal layer of the epidermis. Of these, we examined the expression of CD44, and found that the protein is localized in the innermost basal layers of the composite and, above all, in the epithelial cells in direct contact with Hyaff 11 (benzyl ester of HA), both in the form of non-woven tissue and in the form of microperforated membranes. This suggests that, besides acting as a support for the cells, the biomaterial also interacts with the cells which adhere to it.

Lastly, it is possible to observe the production of specific proteins of the dermoepidermal junction (laminin, collagen, types III, IV and VII), while on the "dermal" side there is abundant production of the extracellular matrix, shown by specific staining and immunohistological methods (see example 1).

For purely indicative purposes, and without being limited by the same, we report here some examples characterising the new-formed tissue.

EXAMPLE 1

A piece of non-woven tissue (1.5×1.5 cm) constituted by Hyaff 11 (benzyl ester of HA) is laid on the bottom of a culture dish and fixed in place at the four corners with fibrin glue. Primary human fibroblasts are seeded on the non-woven tissue ($0.1 \times 10^6$ cells in 0.2 ml of medium) slowly soaking the non-woven tissue. The dish is covered and left to stand for about 30 minutes under a sterile hood, after which the volume is brought to 2 ml with DMEM containing 10% FCS and the dish is incubated at 37° C. in an atmosphere of 5% $CO_2$.

Human kc between the II and IV culture passages are seeded on a Laserskin® membrane measuring $5 \times 5$ cm² (Andreassi et al. Wounds 3:116, 1991). The kc can be cultivated in CEC medium (Rheiwald and Green, Cell, 6:331, 1975) in the presence or in the absence of a feeder-layer but using a chemically defined medium (Andreassi et al. Wounds, 3:116, 1991). Both in fibroblast cultures and in kc cultures, the relative media are changed every 48–72 hours.

Once a well-stratified epithelial layer has been formed, the Laserskin® membrane is cut with a scalpel in sterile conditions, into pieces measuring $1.5 \times 1.5$ cm. The fibroblast culture on the non-woven tissue is laid on a sterile steel net (about 3 mm high); this is then placed in a Petri dish measuring 6 cm in diameter. The epithelial layer is laid on the non-woven tissue, taking care that no air bubbles are trapped in the interface between the two materials (in the example reported here, no adhesives were used to fix the epithelioid membrane to the non-woven tissue).

A medium such as CEC or MCDB 153, suitable for kc growth, is added in a volume which brings the level of the liquid to just below the upper surface of the epithelial layer, but completely soaking the non-woven tissue.

The medium is changed every 72 hours. The first change of medium is supplemented with ascorbic acid (1 $\mu$g/ml). to favour the production of the extracellular matrix. The emergence of the culture is to mimic physiological skin conditions by stimulating complete differentiation of the epithelial cells, as amply reported in the literature (Prunieras et al., J. Invest. Dermatol., 81: 280, 1983: Bernstam et al. in vitro Cell. Biol., 22: 695, 1986). The culture is maintained for 14 days, during which time it is observed by phase-contrast microscopy to check that the epithelial layer expands beyond the edges of the membrane. The material's opacity makes any further observation difficult. At the end of the culture time, the composite material is cut in half with a scalpel, being careful to maintain its structure. One half is treated by traditional histological techniques (hematoxylin-eosin staining), while the other half is immersed in OCT (medium for the cryopreservation of tissues, Milestones, USA), frozen in liquid nitrogen and then stored at –80° C. The latter is cut into 6 $\mu$m thick slices with a cryostat. The slices are used for immunohistochemical investigation, using antibodies against the markers of the differentiation status of the kc, of the dermal-epidermal junction and of the extracellular matrix.

Results of histological hematoxylin-eosin staining

FIG. 1 ($\times 100$) shows a well stratified epithelium over a microperforated Laserskin® membrane. The upper and outer layer is undergoing keratinization. The kc appear to be well distributed on the underside of the membrane, and to have colonized the underlying nonwoven tissue to a considerable extent. The epithelial layer is very compact with a variable thickness which is never less than 10–15 cells. The dividing line between the layer of epithelial cells and underlying fibroblasts can be seen clearly. The cross-sections of fibres from the non-woven tissue are also clearly visible, as is the Laserskin® microperforated membrane.

Immunohistochemical characterization

Studies on the tissue markers were conducted with the following antibodies:
1) anti-keratin antibody KL4 (Dermatology Department, Immacolata, Rome)
2) anti-involucrin polyclonal antibody (Dermatology Department, Immacolata, Rome)
3) anti-human integrin monoclonal antibody β4 (Dermatology Department, Immacolata, Rome)
4) anti-human integrin monoclonal antibody β1 (Dermatology Department, Immacolata, Rome)
5) anti-human CD44 monoclonal antibody (Prof. Abatangelo, Department of Histology and Embryology of the University of Padua)
6) anti-collagen polyclonal antibody III (Chemicon, California USA)
7) anti-collagen polyclonal antibody IV (Sigma)
8) anti-laminin polyclonal antibody (Sigma)
9) anti-fibronectin polyclonal antibody (Sigma)

Figure 2:
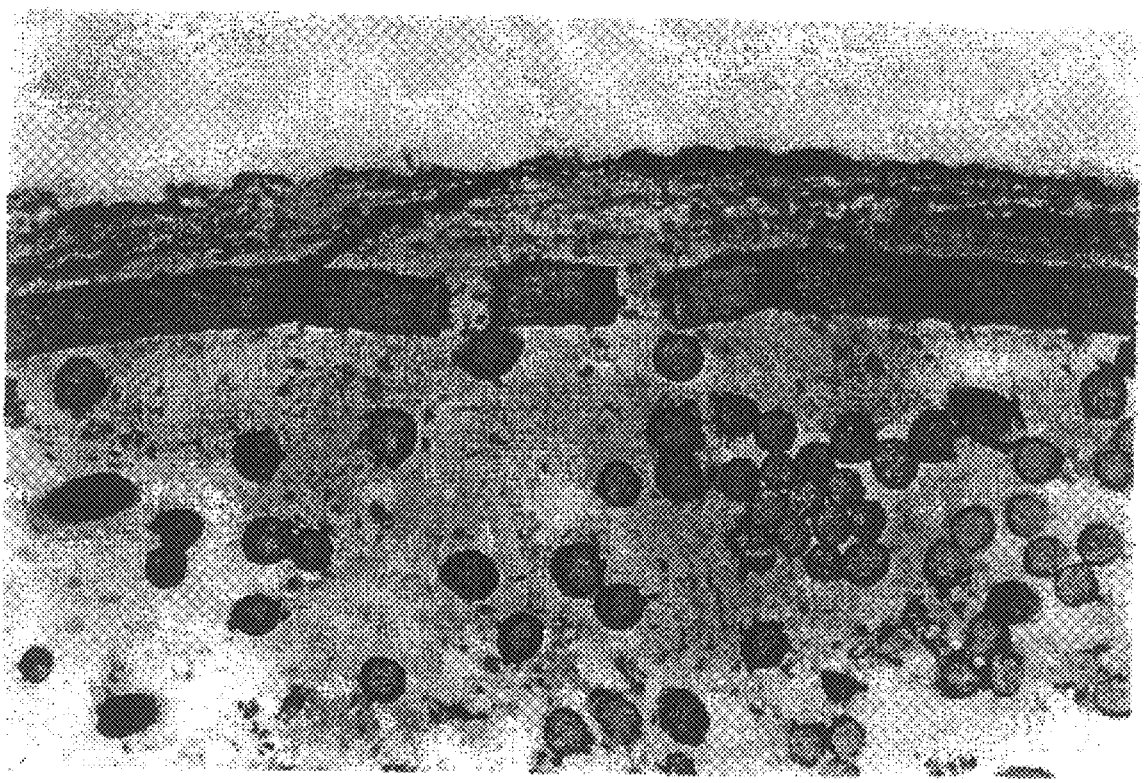
FIG. 2 shows the immunohistochemistry of the composite culture probed with an antiinvolucrin antibody, the outer epithelial layer is undergoing keratinization (×200).
Figure 3:
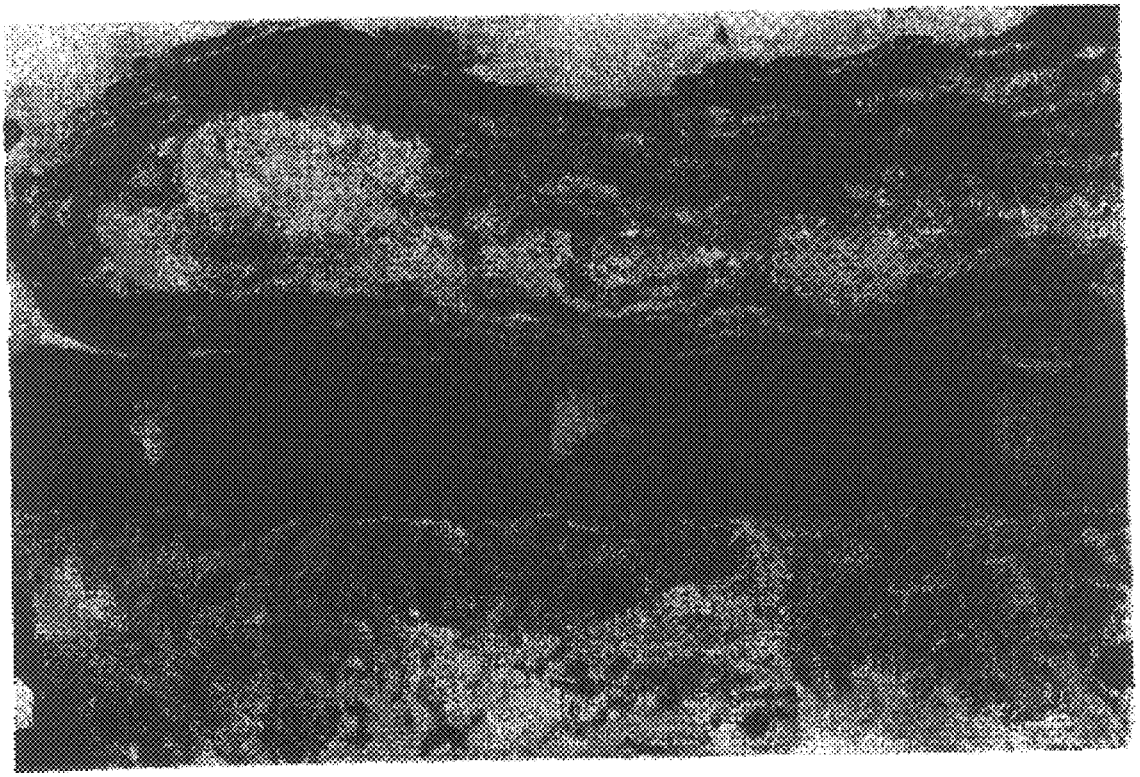
FIG. 3 shows the immunohistochemistry of the composite culture probed with anti-KL4 (total keratin) antibody, a classic Kc marker (×200).
Figure 4A:
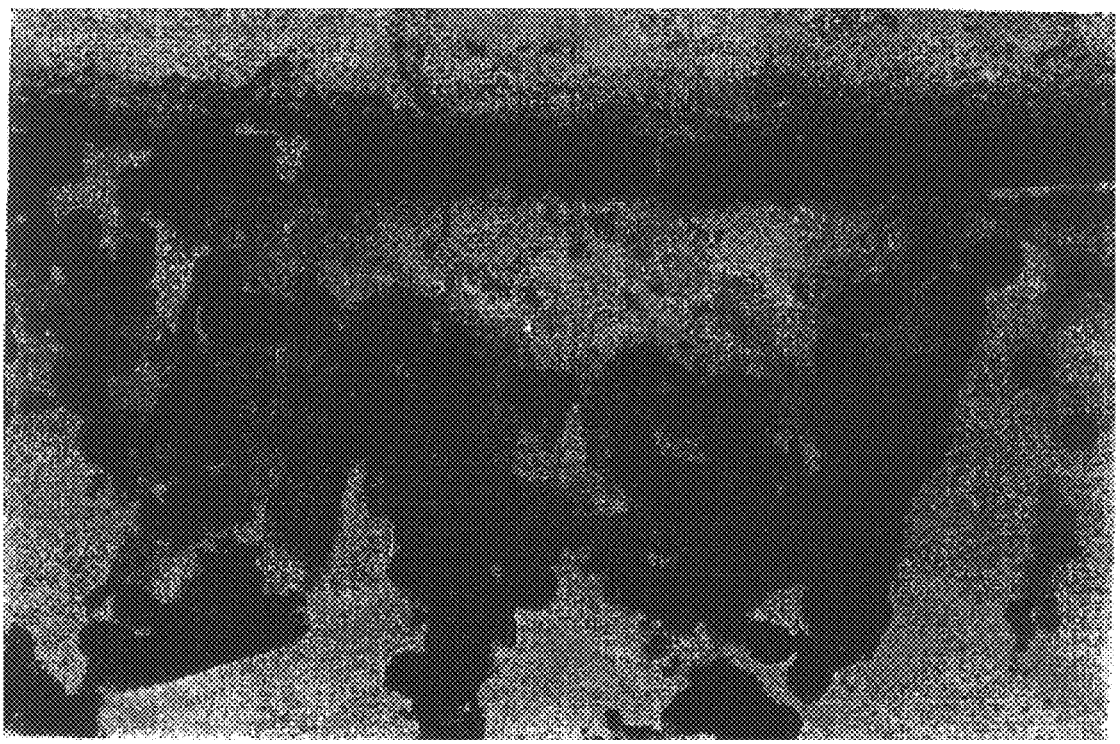
FIG. 4a shows the immunohistochemistry of the composite culture showing the β4 integrin subunits expression, predominantly found in the basal Kc cell layer (×100).
Figure 4B:
FIG. 4b shows the immunohistochemistry of the composite culture showing the β1 integrin subunit mainly expressed at the intercellular bridges joining the epithelial cells (×100).
Figure 5:
FIG. 5 shows the immunolocalization of basal Kcs expressing the CD44 receptor (×200).
Figure 6:
FIG. 6 shows the immunohistochemistry of the composite culture showing the basement-membrane-like zone, as can be seen from the extent of laminin deposition (×200).

Immunohistological investigation reveals that:

a) the outer epithelial layer is well differentiated and undergoing keratinization, as the immunopositivity to involucrin is very marked (FIG. 2, $\times 200$).

b) the compact cell layer on the upper side of the non-woven tissue is constituted by kc, since the response to cytokeratin is very strong here compared to the underlying fibroblastic component (FIG. 3, $\times 200$);

c) the subunits β4 and β1 of the integrins are present in what is essentially a basal layer of the newly-formed tissue. These subunits, and especially β4, are expressed in the epidermis, at the level of the basement membrane, in the structures anchoring the membrane to the underlying dermis (hemidesmosomes). In the "artificial skin" depicted here, the positive β4 cells (FIG. 4a $\times 100$) express the protein predominantly in the basal part, while the integrin β1 is expressed in the intercellular bridges joining the kc (FIG. 4b, $\times 100$). The observations reported here constitute an important indication of the correct "polarization" of the newly formed epidermis.

d) The kc in direct contact with the fibers of the non-woven tissue, like the cells in contact with the top and underside of the Laserskin®, show a marked immunopositivity to CD44 (FIG. 5, $\times 200$). It is thought that this represents a singular feature of the composite culture described here: indeed, CD44 can mediate cell adhesion to the material (constituted by modified hyaluronic acid), and likewise its degradation.

e) In the basement membrane, and therefore also the dermoepidermal junction, a typical extracellular matrix can be observed, the components of which are mainly produced by the basal kc resident in the area. Characteristic markers are therefore laminin and collagen types IV and VII. Confirmation of these observations is given by the fact that the three components are expressed in the interposition between the basal layer of the kc embedded in the non-woven tissue and the underlying fibroblasts. In particular, the extent of the response to laminin (FIG. 6, $\times 200$) is focalized on that which can be considered an "artificial basement membrane".

f) Lastly, on the side of the dermis, a strong immunopositivity to fibronectin can be found. Fibronectin is a protein of the matrix produced by the fibroblasts which are obviously abundant in the dermis. The lack of response in the epidermal layer again indicated that the formation of a well-structured dermal tissue with the typical natural skin structure has been artificially induced.

EXAMPLE 2

In order to demonstrate the possibility of cryopreserving the artificial skin thus produced, the dermal-epidermal cultures are frozen in the presence of a cryopreserving agent such as dimethylsulfoxide (DMSO), according to the usual technique. In short, the culture is lifted and placed on a petri dish measuring 10 cm in diameter and containing 20 ml of freezing medium for (45% DMEM, 45% FCS, 10% DMSO) cooled to 4° C. It is left to reach equilibrium for about 5 minutes, then the dish is brought to a temperature of −80° C. by a process of continuous freezing at a rate of −1° C./min., starting from 4° C.

After one week the "artificial skin" is defrozen, warmed rapidly to 37° C. and the culture is repeatedly washed with DMEM containing 10% FCS, to completely eliminate any residue DMSO. It is left to stand in an incubator at 37° C. for 24 hours (in an atmosphere of 5% $CO_2$), after which the tissue undergoes the histological and immunohistological examination described in Example 1.

Results

No significant morphological and/or structural alterations were observed in the material, compared to before freezing.

These results indicate that the artificial skin described herein can be used to constitute "tissue banks", thanks to its resistance to freezing.

We claim:

1. Artificial human skin comprising:
   a) a microperforated membrane based on a hyaluronic acid derivative, on which keratinocytes have been seeded and cultured,
   b) an underlying non-woven tissue based on a hyaluronic acid derivative wherein fibroblasts have been seeded and left to proliferate.

2. The artificial human skin according to claim 1 further comprising an extracellular protein matrix, containing proteins of the dermoepidermal juntion placed at the interface between fibroblasts and keratinocytes cells.

3. The artificial human skin according to claim 1 wherein said hyaluronic acid derivative used for preparing both the microperforated membrane and the non-woven tissue is an ester of hyaluronic acid.

4. The artificial human skin according to claim 3 wherein said hyaluronic acid ester has a percentage of esterification comprised between 75% and 100%.

5. The artificial human skin according to claim 3 wherein said ester is the hyaluronic benzyl ester.

6. A controlled release medicament containing the artificial human skin according to claim 1, as the vehicling agent, said medicament containing at least one active principle selected from the group consisting of biologically active compounds, proteins peptides and mixture thereof, wherein said active principle is adsorbed to the fibres of the non-woven tissues and/or to the microperforated membrane.

7. The controlled release medicament according to claim 6 wherein said proteins are growth factors, selected from the group consisting of Fibroblast Growth Factors,Transforming Growth Factor β, Keratinocyte Growth Factor, Nerve Growth Factor, or proteins of the extracellular matrix selected from the group consisting of Fibronectin, Laminin, Collagen, or proteins involved in the clotting cascade.

8. The controlled release medicament according to claim 7 wherein said proteins of the extracellular matrix are adsorbed to the fibres of the extracellular matrix.

9. A process for preparing the artificial human skin according to claim 1 comprising the following steps:
   i) seeding keratinocytes cultures at a density ranging from 1,000 to 100,000 cell/cm$^2$, on a microperforated membrane based on a hyaluronic acid derivative and expanding said keratinocytes on said membrane according to conventional techniques involving the use of fetal calf serum until achieving partial or complete confluence,
   ii) cultivating the fibroblasts isolated from the dermis of from other districts by the usual techniques in DMEM containing 10% fetal calf serum, conditioning these fibroblasts to proliferate by seeding on plastic, seeding the fibroblasts in the non-woven tissue and continuing the culture until freezing in case the obtained artificial skin must be preserved or until grafting,
   iii) laying the epithelial layer already formed on the non-woven tissue colonized by fibroblasts, being careful that the outer edge of the microperforated membrane does not touch the bottom of the dish and that it extends slightly beyond the underlying non-woven tissue,
   iv) optionally fixing together the epithelial cells layer on the microperforated membrane to the underlying non-woven tissue colonized by fibroblasts by means of biological adhesives selected from the group consisting of: collagen, fibrin, fibrin glue,
   v) adding a sufficient volume of the same medium used in step (i), keeping the culture immersed so that the keratinocytes of the upper layer of the microperforated membrane are on the air-liquid interface, adding at the first and subsequent changes of medium, ascorbic acid at concentration equal to 1 μg/ml, continuing the culture until graft or freezing.

10. The process according to claim 9 wherein in step (i) the seeding density of keratinocytes cells is comprised between 5,000 and 25,000 cells/cm$^2$, and the cells are expanded in CEC culture medium, in the presence of a "feeder-layer" of nonproliferating 3T3-murine fibroblasts.

11. A process for preparing an artificial human skin according to claim 1 comprising the following steps:
    i') seeding the fibroblasts in the non-woven tissue and continuing the culture until freezing or grafting,
    ii') laying the microperforated membrane on the non-woven tissue, with its edges extending slightly beyond those of the underlying tissue and fixing said membrane with the biological adhesives selected from the group consisting of: collagen, fibrin, fibrin glue or by mechanical means,
    iii') seeding the keratinocytes on the microperforated membranes, expanding said keratynocytes by using a medium, which is suitable for keratinocyte growth on plastic dishes until achieving confluence,
    iv') adding a sufficient volume of the same medium used in the preceding step, the culture immersed so that the keratinocytes of the upper layer of the microperforated membrane are on the air-liquid interface, adding at the first and subsequent changes of medium, ascorbic acid at concentration equal to 1 μg/ml, continuing the culture until grafting.

12. The process according to claim 9, wherein, when the skin must be preserved, it further comprises the step of cryopreservation said artificial skin in the presence of a cryopreservation agent.

13. The process according to claim 9, wherein fibroblasts and keratinocytes come from primary cultures or from frozen stocks.

14. The process according to claim 11 wherein, when the skin must be preserved, it further comprises the step of cryopreservation of said artificial skin in the presence of a cryopreservation agent.

15. The process according to claim 11, wherein fibroblasts and keratinocytes come from primary cultures or from frozen stocks.

16. A surgical method for the treatment of deep II and III degree burns, comprising grafting the artificial skin according to claim 1 to a patient in need of such a treatment.

17. A surgical method for the treatment of ulcers selected from the group consisting of diabetic ulcers, venous ulcers and bed sores, said method comprising grafting the artificial skin according to claim 1 onto the ulcer on a patient in need of such grafting.

18. A surgical method for plastic surgical operations comprising grafting the artificial skin according to claim 1 onto an area on a patient in need of such grafting.

19. The artificial human skin according to claim 1 wherein the keratinocytes, the fibroblasts or both are genetically modified.

20. A surgical method for the treatment of genetic diseases, comprising grafting the artificial skin according to claim 19 onto a patient in need of such grafting.

21. A method for in vitro testing to determine the possible toxic effects of substances to be placed in contact with the skin which comprises contacting the artificial skin of claim 1 with the substance to be tested and observing any change in said artificial skin.

22. A hair graft which comprises the artificial skin of claim 1 in which dermal hair follicle fibroblasts have been cultured along with the keratinocytes.

23. The artificial human skin according to claim 1 which also includes melanocytes.

24. A surgical method for the treatment of diseases characterized by melanin deficiency said method comprising grafting the artificial human skin according to claim 23 onto a patient having a melanin deficiency.

\* \* \* \* \*